(12) United States Patent
Chen et al.

(10) Patent No.: US 7,291,470 B2
(45) Date of Patent: *Nov. 6, 2007

(54) **PRIMER COMPOSITION AND METHOD OF USING THE SAME IN THE DETECTION OF *SHIGELLA SONNEI***

(75) Inventors: Jiann-Hwa Chen, Taichung (TW); Wen-Bin Hsu, Taichung (TW); Pei-Chum Chen, Taichung (TW)

(73) Assignee: National Chung-Hsing University, Taiwan (TW)

( * ) Notice: Subject to any disclaimer, the term of this patent is extended or adjusted under 35 U.S.C. 154(b) by 32 days.

This patent is subject to a terminal disclaimer.

(21) Appl. No.: 11/213,665

(22) Filed: Aug. 26, 2005

(65) Prior Publication Data

US 2006/0110749 A1 May 25, 2006

Related U.S. Application Data

(63) Continuation-in-part of application No. 10/200,927, filed on Jul. 23, 2002, now Pat. No. 6,955,880.

(51) Int. Cl.
*C12Q 1/68* (2006.01)

(52) U.S. Cl. .................. 435/6; 435/91.1; 435/91.2; 536/24.33

(58) Field of Classification Search ............ None
See application file for complete search history.

(56) References Cited

U.S. PATENT DOCUMENTS 5,958,686 A 9/1999 Houng

OTHER PUBLICATIONS

Houng, H.H. et al. "A Simple Polymerase Chain Reaction Technique To Detect And Differentiate *Shigella* And Enteroinvasive *Escherichia coli* in Human Feces." Diagn Microbiol Infect Dis. (1997) 28 pp. 19-25.

*Primary Examiner*—Jeffrey Fredman
*Assistant Examiner*—Heather Calamita
(74) *Attorney, Agent, or Firm*—Ladas & Parry LLP

(57) ABSTRACT

The invention provides a new primer composition for detecting the presence of *Shigella sonnei* and a method of using the same. The primer composition and method have high specificity and sensitivity on the detection of *Shigella sonnei*. The invention also provides a method for extracting the nucleic acids of microorganisms in a solution sample.

12 Claims, 14 Drawing Sheets

(A)

(B)

(A)

(B)

(a)

(b)

(a)

(b)

(c)

(d)

(A)

(B)

(a)

(b)

(a)

(b)

(c)

(d)

(A)

(B)

SEQUENCE LISTING

<160> NUMBER OF SEQ ID NOS: 8

<210> SEQ ID NO 1
<211> LENGTH: 16
<212> TYPE: DNA
<213> ORGANISM: Artificial Sequence
<220> FEATURE:
<223> OTHER INFORMATION: Primer for amplifying DNA of Shigella sonnei

<400> SEQUENCE: 1
atgccgggca actgca                                                    16

<210> SEQ ID NO 2
<211> LENGTH: 16
<212> TYPE: DNA
<213> ORGANISM: Artificial Sequence

```
<220> FEATURE:
<223> OTHER INFORMATION: Primer for amplifying DNA of Shigella sonnei

<400> SEQUENCE: 2
ctgcgtatat cgcttg                                                    16

<210> SEQ ID NO 3
<211> LENGTH: 20
<212> TYPE: DNA
<213> ORGANISM: Artificial Sequence
<220> FEATURE:
<223> OTHER INFORMATION: Primer for amplifying DNA of Mycobacterium
      tuberculosis

<400> SEQUENCE: 3
cctgcgagcg taggcgtcgg                                                20

<210> SEQ ID NO 4
<211> LENGTH: 20
<212> TYPE: DNA
<213> ORGANISM: Artificial Sequence
<220> FEATURE:
<223> OTHER INFORMATION: Primer for amplifying DNA of Mycobacterium
      tuberculosis

<400> SEQUENCE: 4
ctcgtccagc gccgcttcgg                                                20

<210> SEQ ID NO 5
<211> LENGTH: 18
<212> TYPE: DNA
<213> ORGANISM: Artificial Sequence
<220> FEATURE:
<223> OTHER INFORMATION: Primer for amplifying DNA of Shigella spp. and
      Enteroinvasive E. coli

<400> SEQUENCE: 5
ctggatggta tggtgagg                                                  18

<210> SEQ ID NO 6
<211> LENGTH: 20
<212> TYPE: DNA
<213> ORGANISM: Artificial Sequence
<220> FEATURE:
<223> OTHER INFORMATION: Primer for amplifying DNA of Shigella spp. and
      Enteroinvasive E. coli

<400> SEQUENCE: 6
ggaggccaac aattatttcc                                                20

<210> SEQ ID NO 7
<211> LENGTH: 20
<212> TYPE: DNA
<213> ORGANISM: Artificial Sequence
<220> FEATURE:
<223> OTHER INFORMATION: Primer for amplifying DNA of Heliobacter pylori

<400> SEQUENCE: 7
taacaaaccg ataatggcgc                                                20

<210> SEQ ID NO 8
<211> LENGTH: 20
<212> TYPE: DNA
<213> ORGANISM: Artificial Sequence
```

```
-continued

<220> FEATURE:
<223> OTHER INFORMATION: Primer for amplifying DNA of Heliobacter pylori

<400> SEQUENCE: 8
catcttgtta gagggattgg                                                    20
```

PRIMER COMPOSITION AND METHOD OF USING THE SAME IN THE DETECTION OF SHIGELLA SONNEI

This is a continuation-in-part of application Ser. No. 10/200,927 filed on Jul. 23, 2002 now U.S. Pat. No. 6,955,880, and claims the benefit thereof and incorporates the same by reference.

FIELD OF THE INVENTION

The present invention relates to a new primer composition and a method of using the primer composition in the detection of Shigella sonnei.

BACKGROUND OF THE INVENTION

The detection of microorganisms in environmental water or drinking water is very important to environmental sanitation and public health. There is a need in detecting pathogens in environmental water or drinking water effectively and rapidly such as the detection of Escherichia coli, Staphylococcus aureus, Salmonella spp., Vibrio cholerae, Helicobacter pylori, Shigella sonnei, Legionella spp., Pseudomonas aeruginosa and Enterovirus.

Organisms of the genus Shigella cause classic bacillary dysentery that is characterized by severe diarrhea, fever and abdominal pain. Shigella is one of Enterobacteriacea and can be classified into four species: S. dysenteriae, S. flexneri, S. boydii and S. sonnei. Shigella spp. is typically associated with self-limiting infections that are rarely fatal except in children or the elderly. Infection with S. dysenteriae can cause a severe form of the disease with up to 20% of cases proving fatal, such as hemorrhagic colitis and hemolytic uremic syndrome. Although the syndromes caused by the infection with S. flexneri, S. boydii and S. sonnei are not so severe and can be cured by antibiotics, the general use of antibiotics results in the production of strains resistant against antibiotics. Moreover, S. sonnei infection frequently occurs in the industrially developed area. The S. sonnei infection will be popular in the industrial area of a high population density. Normally, the human by intake of 10–100 bacteria cells will be infected (DuPont et al., 1989, J. infect. Dis.).

Traditionally, two methods are used in the detection of microorganisms in solution samples. One is directed to a method comprising the steps of filtering a water sample by a filter, culturing the filter in a petri dish and then observing the appearance of the colonies and calculating the numbers of the colonies. The other one is directed to a biochemical analysis method comprising the steps of culturing the samples with a medium broth, using specific agents to carry out a biochemical reaction with the microbial cultures and then analyzing the results of the biochemical reaction. Recently, polymerase chain reaction (PCR) methods and hybridization methods are developed to detect the microorganisms in water samples, which require extracting the nucleic acids of the microorganism from the samples. Bej et al. disclose a method of filtering a solution sample with a filter, adding the filter to sterile water and then shaking and treating the filter with a mixed liquid containing ethanol and dry ice (ethanol-dry ice bath) and warm water (45 to 50° C.) alternatively for five times (Applied and Environmental Microbiology, April 1991, 57(4): 1013–1017). However, since the method needs an alternative treatment with high temperature and low temperature, it is complicated and time-consuming.

Morris et al. indicated that the isolation percent of Shigella spp. samples was lower than 25%. That is, more than 75% of samples existing Shigella spp. could not be correctly detected (Morris et al., 1970, Appl. Microbiol.). Polymerase chain reaction (PCR) can be rapid and reliable for detecting bacteria and virus in various samples. It was described in Josephson et al., 1993, App. Environ. Microbiol that the PCR can detect the S. sonnei that cannot be cultivated. However, the method cannot specifically detect the existence of S. sonnei. Accordingly, there is a need to provide a method for a rapid and specific detection of S. sonnie in food and clinical samples and an improvement method for extracting the nucleic acids of microorganisms in a solution sample.

SUMMARY OF THE INVENTION

One object of the invention is to provide a primer composition that amplifies a 369 base pair DNA of Shigella sonnei, said composition comprising the primers IS1SS and IS1SR3 wherein the primer IS1SS comprises the sequence as defined in SEQ ID NO:1 and the primer IS1SR3 comprises the sequence as defined in SEQ ID NO:2.

Another object of the invention is to provide a method for detecting Shigella sonnei in a solution sample, which comprises the following steps:

(a) incubating said sample with primers IS1SS and IS1SR3 in a PCR reaction solution whereby a PCR reaction takes place and amplifies nucleic acids to produce a 369 base pair amplification product;

(b) detecting the presence of a 369 base pair amplification product;

(c) splicing the 369 base pair amplification product by restriction enzyme BstEII;

(d) detecting the presence of the DNA fragments of the 78 base pair and 291 base pair; wherein the presence of said DNA fragments are indicative of the presence of Shigella sonnie in the sample.

A further object of the invention is to provide a method for extracting the nucleic acids of microorganisms in a solution sample, which comprises the following steps:

(a) passing a solution sample through a filter membrane so that the microorganisms therein attach on the surface of the filter membrane;

(b) placing the filter membrane into a solution; and (c) heating the resulting solution to lyse the microorganisms so that their nucleic acids are released to the solution.

(south 36) diluted by $10^{11}$ times; Lane 5: sterile water; Lane 6: *S. sonnei* (ATCC 29930) diluted by $10^6$ times; Lane 7: 100 bp marker.

Figure 10:
Figure 10:
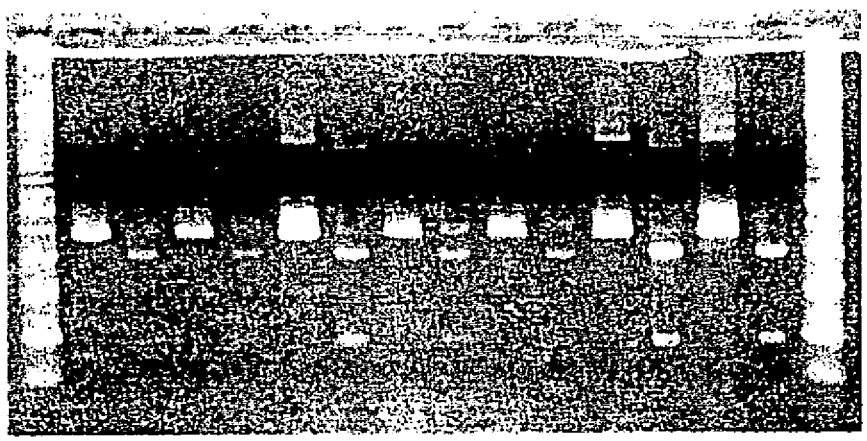

FIG. 10 shows the electrophoresis plot of the BstEII sliced fragments of the 369 bp products of *S. sonnei*, the lanes of odd numbers represent the PCR products that were not cut by the BstEII and the lanes of even numbers represent the PCR products that were cut by the BstEII; (A) Lane M: 100 bp marker; Lanes 1 and 2: *S. sonnei* (ATCC 11060); Lanes 3 and 4: *S. sonnei* (ATCC 25931); Lanes 5 and 6: *S. sonnei* (ATCC 20920); Lanes 7 and 8: *S. sonnei* (ATCC 29031); Lanes 9 and 10: *S. sonnei (south* 27); (B) Lane M: 100 bp marker; Lanes 1 and 2: *S. sonnei* (south 36); Lanes 3 and 4: *S. sonnei* (SH 10567); Lanes 5 and 6: *S. sonnei* (SH 7105); Lanes 7 and 8: *S. sonnei* (SH 8255); Lanes 9 and 10: *S. sonnei* (SH 9397); Lanes 11 and 12: *S. sonnei* (SH 8069); Lanes 13 and 14: *S. sonnei* (ATCC 9290).

Figure 11:
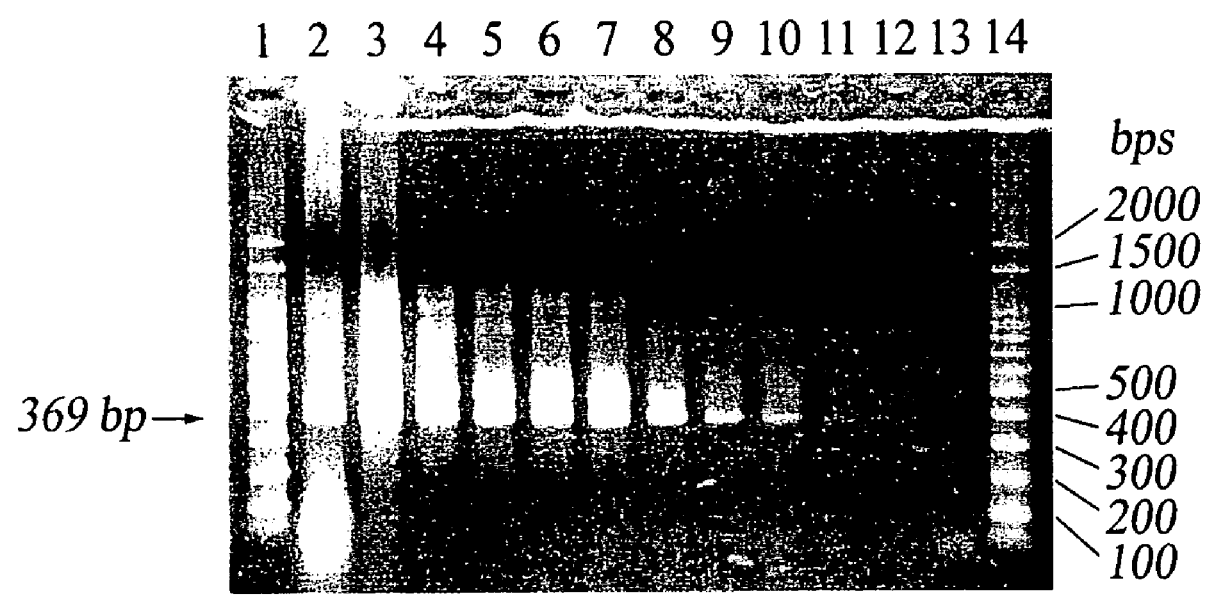

FIG. 11 shows the results of PCR reaction of the diluted solutions of *S. sonnei*; Lane 1: 100 bp marker; Lane 2: 10 times dilution; Lane 3: $10^2$ times dilution; Lane 4: $10^3$ times dilution; Lane 5: $10^4$ dilution; Lane 6: $10^5$ times dilution; Lane 7: $10^6$ times dilution; Lane 8: $10^7$ times dilution; Lane 9: $10^8$ times dilution; Lane 10: $10^9$ times dilution; Lane 11: $10^{10}$ times dilution; Lane 12: $10^{11}$ times dilution; Lane 13: sterile water; and Lane 14: 100 bp marker.

Figure 2:
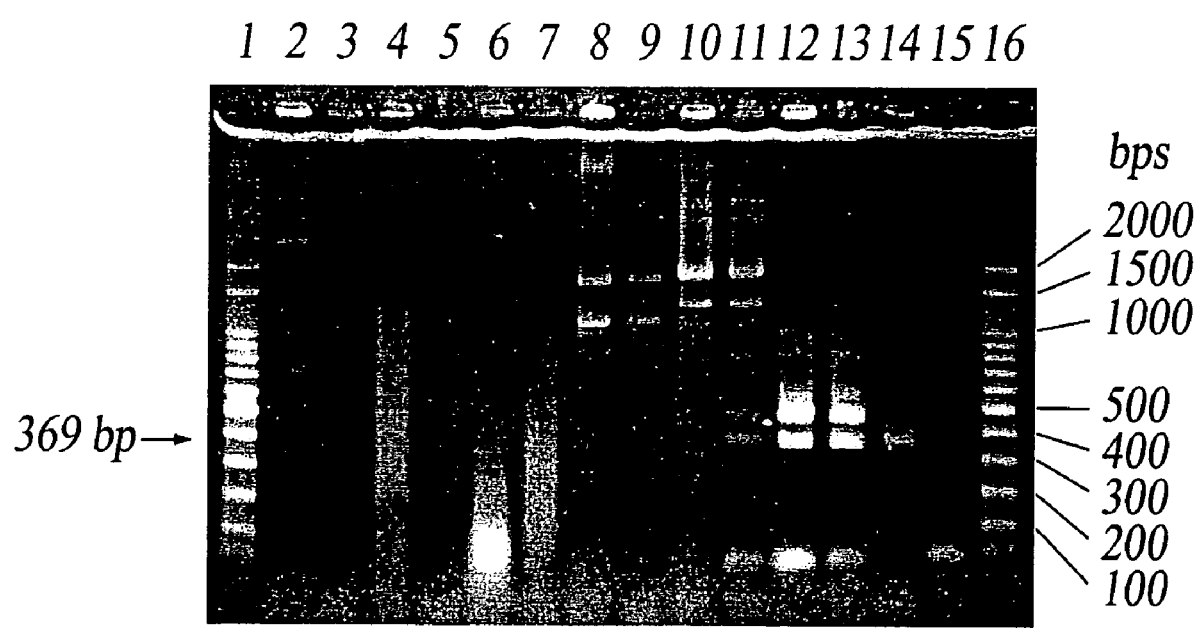
FIG. 2 shows the electrophoresis plot of the samples of Escherichia coli W3110 (ATCC 27325), Sallmonella choleraesuis (ATCC 13311), Klebsiella pneumoniae (ATCC 13883), Serratia marcescens (ATCC 13880), Enterobacter aerogenes (ATCC 13048) and Enterobacter cloacae (ATCC 13047); Lane 1: 100 bp marker; Lane 2: Klebsiella pneumoniae diluted by $10^2$ times; Lane 3: Klebsiella pneumoniae diluted by $10^3$ times; Lane 4: Sallmonella choleraesuis diluted by $10^2$ times; Lane 5: *Sallmonella choleraesuis* diluted by $10^3$ times; Lane 6: *Serratia marcescens* diluted by $10^2$ times; Lane 7: *Serratia marcescens* diluted by $10^3$ times; Lane 8: *Enterobacter cloacae* diluted by $10^2$ times; Lane 9: *Enterobacter cloacae* diluted by $10^3$ times; Lane 10: *Enterobacter aerogenes* diluted by $10^2$ times; Lane 11: *Enterobacter aerogenes* diluted by $10^3$ times; Lane 12: *Escherichia coli* W3110 diluted by $10^2$ times; Lane 13: *Escherichia coli* W3110 diluted by $10^3$ times; Lane 14: *S. flexneri* diluted by $10^2$ times; lane 15: sterile water; Lane 16: 100 bp marker.
Figure 12:
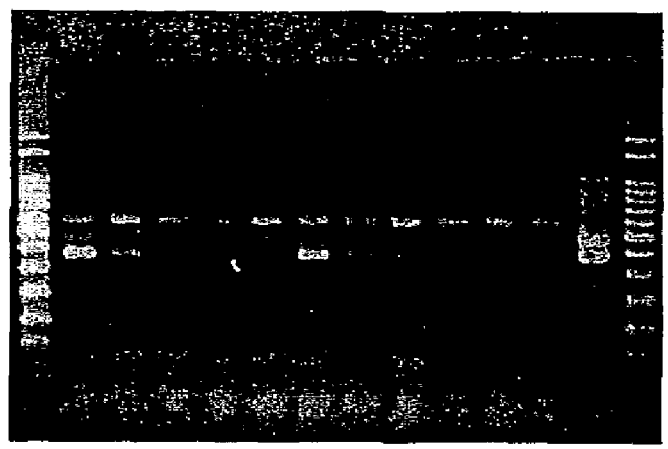
Figure 12:

FIGS. 12(*a*) and (*b*) show the results of PCR reaction of the diluted solutions of *S. sonnei* ATCC 9290, ATCC 11060, ATCC 25931, ATCC 20920 and ATCC 29031; FIG. 12(*a*): Lane 1: 100 bp marker; Lanes 2 to 6: *S. sonnei* ATCC 9290 diluted by $10^7$, $10^8$, $10^9$ and $10^{10}$ times, respectively; Lanes 7 to 11: *S. sonnei* ATCC 11060 diluted by $10^7$, $10^8$, $10^9$ and $10^{10}$ times, respectively; Lane 12: sterile water; Lane 13: *S. sonnei* ATCC 29930 diluted by $10^6$ times; and Lane 14: 100 bp marker; FIG. 2(*b*): Lane 1: 100 bp marker; Lanes 2 to 4: *S. sonnei* ATCC 25931 diluted by $10^8$, $10^9$, $10^{10}$ and $10^{10}$ times, respectively; Lanes 5 to 9: *S. sonnei* ATCC 20920 diluted by $10^6$, $10^7$, $10^8$, $10^9$ and $10^{10}$ times, respectively; Lane 10: sterile water; Lanes 11 to 13: *S. sonnei* ATCC 29031 diluted by $10^8$, $10^9$ and $10^{10}$ times; Lane 14: sterile water; Lane 15: *S. sonnei* ATCC 29930 diluted by $10^6$ times and Lane 16: 100 bp marker.

Figure 13:
Figure 13:
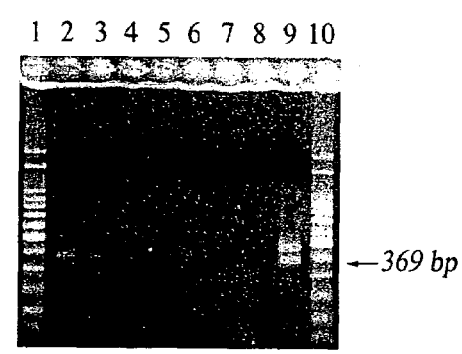
Figure 13:
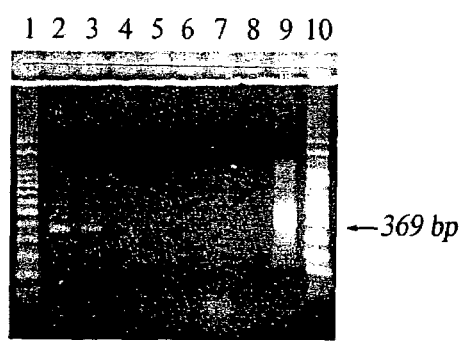
Figure 13:
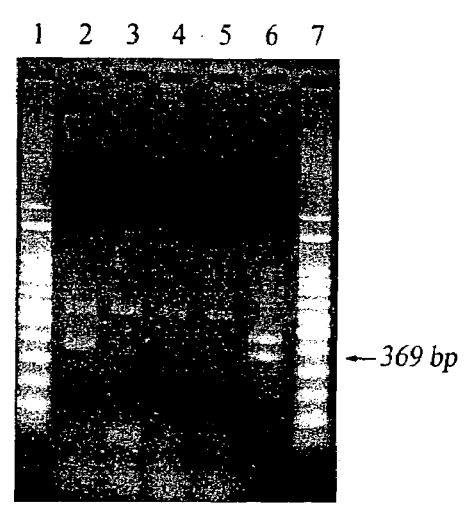

FIGS. 13(*a*) to (*d*) show the results of PCR reaction of using the diluted solutions of *S. sonnei* SH 7105, SH 8069, SH 8255, SH 9397, SH 10567, south 27 and south 36 as templates and IS1SS and IS1SR3 as primers; FIG. 13(*a*): Lane 1: 100 bp marker; Lane 2: *S. sonnei* diluted by $10^6$ times; Lanes 3 to 5: *S. sonnei* SH 7105 diluted by $10^8$, $10^9$ and $10^{10}$ times, respectively; Lanes 6 to 8: *S. sonnei* SH 8255 diluted by $10^8$, $10^9$, $10^{10}$ times, respectively; Lane 9: sterile water; Lanes 10 to 12: *S. sonnei* SH 9397 diluted by $10^8$, $10^9$ and $10^{10}$ times, respectively; Lanes 13 to 15: *S. sonnei* SH 8069 diluted by $10^8$, $10^9$ and $10^{10}$ times, respectively; Lane 16: sterile water and Lane 17: 100 bp marker; FIG. 13(*b*): Lane 1: 100 bp marker; Lanes 2 to 7: *S. sonnei* SH 10567 diluted by $10^7$, $10^8$, $10^9$, $10^{10}$ and $10^{11}$ times, respectively; Lane 8: sterile water; Lane 9: *S. sonnei* ATCC 29930 diluted by $10^6$ times; Lane 10: 100 bp marker; FIG. 13(*c*): Lane 1: 100 bp marker; Lanes 2 to 7: *S. sonnei* south 27 diluted by $10^6$, $10^7$, $10^8$, $10^9$, $10^{10}$ and $10^{11}$ times, respectively; Lane 8: sterile water; Lane 9: *S. sonnei* ATCC 29930 diluted by $10^6$ times; Lane 10: 100 bp marker; FIG. 13(*d*): Lane 1: 100 bp marker; Lanes 2 to 4: *S. sonnel south* 36 diluted by $10^9$, $10^{10}$ and $10^{11}$ times, respectively; Lane 5: sterile water; Lane 6: *S. sonnei* ATCC 29930 diluted by $10^6$ times; Lane 7: 100 bp marker.

Figure 14:
Figure 14:
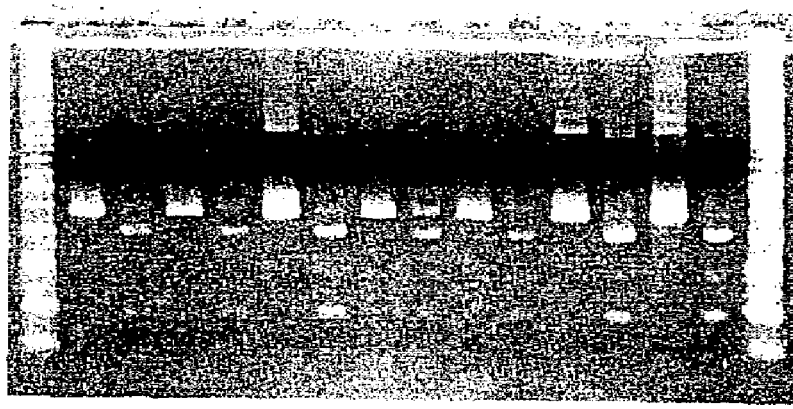

FIGS. 14(*a*) and (*b*) show the electrophoresis plot of the 369 bp PCR products cut with restriction enzyme BstEII of the diluted solutions of *S. sonnei* ATCC 9290, ATCC 11060, ATCC 25931, ATCC 20920, ATCC 29031, SH 7105, SH 8069, SH 8255, SH 9397, SH 10567, south 27 and south 36; FIG. 14(*a*): M: 100 bp marker; Lanes 1 and 2: *S. sonnei* ATCC 11060; Lans 3 and 4: *S. sonnei* ATCC 25931; Lanes 5 and 6: *S. sonnei* ATCC 20920; Lanes 7 and 8: *S. sonnei* ATCC 29031; Lanes 9 and 10: *S. sonnei* south 27; FIG. 14(*b*): M: 100 bp marker; Lanes 1 and 2: *S. sonnei* south 36; Lanes 3 and 4: *S. sonnei* SH 10567; Lanes 5 and 6: *S. sonnei* SH 7105; Lanes 7 and 8: *S. sonnei* SH 8255; Lanes 9 and 10: *S. sonnei* SH 9397; Lanes 11 and 12: *S. sonnei* SH 8069; Lanes 13 and 14: *S. sonnei* ATCC 9290.

DETAILED DESCRIPTION OF THE INVENTION

The invention provides a new primer composition for detecting the presence of *Shigella sonnei* and a kit and method of using the same. The invention also provides a method of for extracting the nucleic acids of microorganisms in a solution sample.

Primer Composition for Detection the Presence of *Shigella Sonnei*

One object of the invention is to provide a primer composition that amplifies a 369 base pair DNA of *Shigella sonnei*, said composition comprising the primers IS1SS and IS1SR3 wherein the primer IS1SS comprises the sequence as defined in SEQ ID NO:1 and the primer IS1SR3 comprises the sequence as defined in SEQ ID NO:2.

According to the invention, the term "primer" as used herein refers to an oligonucleotide, whether occurring naturally as in a purified restriction digest or produced synthetically, which is capable of acting as a point of initiation of synthesis when placed under conditions in which synthesis of a primer extension product which is complementary to a nucleic acid strand is induced, i.e. in the presence of nucleotides and an inducing agent such as DNA polymerase and at a suitable temperature and pH. The primer composition of the invention comprises the primers IS1SS and IS1SR3. The sequences of the primers IS1SS and IS1SR3 are as follows:

| IS1SS: | 5'-ATGCCGGGCAACTGCA-3' | (SEQ ID NO: 1) |
| IS1SR3: | 5'-CTGCGTATATCGCTTG-3' | (SEQ ID NO: 2) |

According to the invention, the primers IS1SS and IS1SR3 typically comprise 16 nucleotides, respectively. The IS1SS and IS1SR3 amplify a 369 base pair DNA of *Shigella sonnei*. A length of the primers IS1SS and IS1SR3 is variable as long as they maintain their original function. As nucleic acids do not require complete complementarity in order to hybridize, it is to be understood that the primer sequences herein disclosed may be modified to some extent without loss of utility as the 369 base pair DNA-specific primers. As is known in the art, a hybridization of complementary or partially complementary nucleic acid sequences may be obtained by adjustment of the hybridization conditions to increase or decrease stringency (i.e., adjustment of hybridization pH, temperature or salt content of the buffer). Such minor modifications of the disclosed sequences and any necessary adjustments of hybridization conditions to maintain the 369 base pair DNA-specificity require only routine experimentation and are within the ordinary skill in the art. For example, for diagnostics applications, depending on the complexity of the target sequence, the oligonucleotide primer typically contains 15–25 or more nucleotides, although it may contain fewer nucleotides. For other applications, the oligonucleotide primer is typically shorter, e.g., 7–15 nucleotides.

The primers IS1SS and IS1SR3 of the primer composition of the present invention can be used in various ratios in detection of the *S. sonnei*. Ratios selected will depend upon several factors, including the method of detection used, the amount of nucleic acid material and the source of the biological sample. Preferably, the ratio of IS1SS to IS1SR3 is 1:1.

Primers are readily synthesized by standard techniques. Detailed procedures for the phospho-triester and hydrogen phosphonate methods of oligonucleotide synthesis are described in the U.S. Pat. Nos. 4,458,066.

Method for Detecting *Shigella sonnei* in a Solution Sample

Another object of the invention is to provide a method for detecting *Shigella sonnei* in a solution sample, which comprises the following steps:

(a) incubating said sample with primers IS1SS and IS1SR3 in a PCR reaction solution whereby a PCR reaction takes place which amplifies nucleic acids to produce a 369 base pair amplification product;

(b) detecting the presence of a 369 base pair amplification product;

(c) splicing the 369 base pair amplification product by restriction enzyme BstEII;

(d) detecting the presence of the DNA fragments of the 78 base pair and 291 base pair; wherein the presence of said DNA fragments are indicative of the presence of *Shigella sonnie* in the sample.

According to the invention, any suitable solution sample can be applied in the method of the invention. In particular, water sample containing less amount bacteria also can be applied in the method of the invention.

According to the invention, the method, before the above-mentioned step (a), further comprises a step of filtering the solution sample with a membrane and treating the membrane at a temperature for a time period that is sufficient to lyse the bacteria in said solution. Preferably, the temperature in the method ranges from 85° C. to 97° C. and said time period ranges from 1 to 15 minutes.

According to the invention, any amplification protocol that utilizes cyclic, specific hybridization of primers to the target sequence, extension of the primers using the target sequence as a template and separation or displacement of the extension products from the target sequence may employ in the PCR reaction of the method of the invention. For amplification methods that do not require specialized, non-target binding sequences, the amplification primers may consist only of the target binding sequences of the amplification primers of the invention. As thermocycling is a feature of amplification by PCR, the restriction endonuclease is preferably added at low temperature after the final cycle of primer annealing and extension for end-point detection of amplification. Once amplified, the products can be analyzed by many techniques known in the art. For example, one technique uses physical separation of the amplification products to distinguish the products, such as electrophoresis, chromatograph and filtration. The preferred physical separation is electrophoresis.

According to the invention, the primers IS1SS and IS1SR3 amplify nucleic acids to produce a 369 base pair amplification product. Then, a restriction enzyme BstEII is used to splice the resulting 369 base pair amplification product. The presence of *Shigella sonnie* in the sample can be ensured when the DNA fragments of 78 base pair and 291 base pair are produced after splicing.

According the invention, the method of the invention has 100% specific detection for the *Shigella sonnie*.

Method for Extracting the Nucleic Acids of Microorganisms from a Solution Sample A further object of the invention is to provide a method for extracting the nucleic acids of microorganisms from a solution sample, which comprises the following steps:

(a) passing a solution sample through a filter membrane so that the microorganisms therein attach to the surface of the filter membrane;

(b) placing the filter membrane into a solution; and (c) heating the resulting solution to lyse the microorganisms so that their nucleic acids are released to the solution.

The method of the invention provides a simple and efficient method of extracting nucleic acid of microorganism from liquid samples.

The samples suitable for the method of the invention can be any liquid samples, including tap water, ground water, wastewater, drinking water, juice and soup. The filter membrane suitable for the method of the invention can be any filter membrane that filters microorganism from the liquid samples. In other words, the pores of the filter membrane have to be smaller than the test microorganism. Hence, the choice of the size of the pore would depend on the size of the test microorganism; for example, bacteria would use filter with a pore size of 1–0.1 micrometer, while viruses, which are smaller, would use filter with a pore size of 0.1–0.001 micrometer. The material of the filter membrane could be any material that is suitable for filtering microorganism (i.e. cellulose ester, polyethylene (PE), polypropylene (PP), Polyvinyl Chloride (PVC)). Preferably, the filter membrane used in the method of the invention is coated with a coating so that the microorganisms adsorbed on the filter can be easily removed from the filter membrane through simple physical treatment. The term "physical treatment" used herein refers to the treatment of not using chemical agents, such as shaking or stirring. Preferably, the coating in the filter membrane used in the method of the invention is polytetrafluoroethylene. In one embodiment of the invention, the filter membrane used in the invention is a polyester of polytetrafluoroethylene (i.e. Fluoropore Membrane Filter produce by Millipore Inc).

The step a) of the method of the invention is to pass the liquid medium containing the microorganism through the filter membrane so that the microorganisms can attach to the surface of the filter. This step can be performed with a device loading the filter membrane (i.e. syringe). After filtration, in step (b), the filter membrane is removed and then placed in a solution. The solution can be any liquid suitable for preserving nucleic acids, such as water or buffer solution (i.e. TE buffer (Tris-EDTA buffer) or phosphate buffered saline (PBS)). Optionally, the filter membrane placid in the solution can be physically treated for extra time to speed up the movement of the microorganisms to be separated from the filter membrane and transferred into the solution. In one embodiment of the invention, the filter membrane in the solution is vortex for more than 1 minute, preferably more than 3 minutes but no more than 15 minutes. In step (c), the filter membrane in the solution is heated so that the nucleic acids can be released from the microorganisms into the liquid medium. According to the invention, the filter membrane is heated at a temperature sufficient to lyse the microorganisms attached on the filter membrane to allow the nucleic acids to be released from the microorganisms, preferably more than 80° C. and more preferably more than 85° C. In one preferred embodiment of the invention, the filter membrane is heated at a temperature from 85° C. to 97° C. for 1 to 15 minutes, preferably at a temperature of 94° C. for 5 minutes.

The invention further provides an application of the above-mentioned method, which is directed to the combination of the above-mentioned method for extracting the nucleic acids of microorganisms and a molecular biology assay. The molecular biology assay suitable for used in the invention includes PCR or hybridizing assay. In one embodiment of the invention, the molecular biology assay is PCR that uses a primer specific to the test microorganism. The synthesis and design of primers and PCR assay are known in the art (U.S. Pat. No. 4,458,066 and Sambrook et al., Molecular Cloning: A Laboratory Manual, second edition, 1989, Cold Spring Harbor Laboratory Press).

In one preferred embodiment of the invention, the method of the invention can be used in the detection of the existence of pathogenic microorganisms such as *Escherichia. coli, Staphylococcus aureus, Salmonella* spp, *Vibrio. cholerae, Heliobacter pylori, Mycobacterium tuberculosis, Shigella sonnei, Legionella* spp, *Pseudomonas aeruginosa,* and Enterovirus in liquid samples. Many primers (especially the primer to identify pathogenic microorganism) has already been developed and used with PCR analysis. Examples of the primers used in PCR are as follows:

| Microorganism Species | Primer (5'→3') | |
|---|---|---|
| *Mycobacterium tuberculosis* | CCTGCGAGCGTAGGCGTCGG | (SEQ ID NO:3) |
| | CTCGTCCAGCGCCGCTTCGG | (SEQ ID NO:4) |
| *Shigella* spp. and EIEC | CTGGATGGTATGGTGAGG | (SEQ ID NO:5) |
| (Enteroinvasive *E. coli*) | GGAGGCCAACAATTATTTCC | (SEQ ID NO:6) |
| *Heliobacter pylori* | TAACAAACCGATAATGGCGC | (SEQ ID NO:7) |
| | CATCTTGTTAGAGGGATTGG | (SEQ ID NO:8) |

The inventor of the method mentioned previously has developed two primers specific to *Shigella sonnei*, i.e., IS1SS (5'-ATGCCGGGCAACTGCA-3'; SEQ ID NO:1) and IS1SR3 (5'-CTGCGTATATCGCTTG-3'; SEQ ID NO:2). Using primers specific to a certain species or strain of microorganism can amplify the nucleic acids with specific length of the specific microorganism, thereby the existence of the specific microorganism in a sample can be determined.

In one embodiment of the invention, the method of the invention further comprises a step of using a specific primer to conduct PCR assay. In one preferred embodiment of the invention, the method of the invention uses the primers specific to *Shigella sonnei* (IS1SS and IS1SR3) to amplify 369 bp fragment of *Shigella sonnei*. In the embodiment, by using the method of the invention, a positive reaction can be observed in a solution sample containing 3.4 bacteria per 50 ml, thus displaying the high sensitivity of the method of the invention. In addition, optionally, the 369 bp fragment can be further cut with a restriction enzyme to increase the specificity of the detection. In one preferred embodiment of the invention, the expected 78 bp and 291 bp fragments can be obtained by using BstEII to cut the 369 bp fragment to prevent pseudo positive reaction and increase the specificity of the method of the invention.

While the invention is described above in relation to certain specific embodiments, it will be understood that many variations are possible, and that alternative materials and reagents can be used without departing from the invention. In some cases such variations and substitutions may require some experimentation, but will only involve routine testing.

EXAMPLES

Example 1

Figure 1:
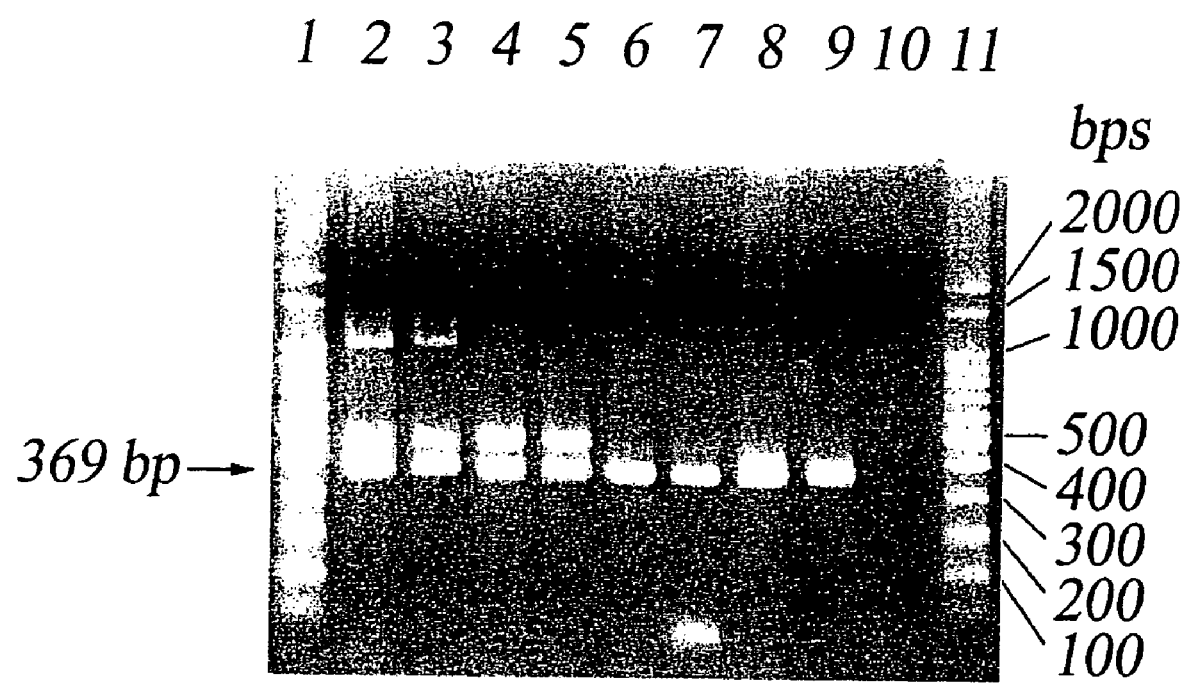
FIG. 1 shows the electrophoresis plot of the samples of the S. boydii, S. dysenteriae, S. flexneri and S. sonnei; Lane 1: 100 bp marker; Lane 2: S. sonnei diluted by $10^2$ times; Lane 3: S. sonnei diluted by $10^3$ times; Lane 4: S. dysenteriae diluted by $10^2$ times; Lane 5: S. dysenteriae diluted by $10^3$ times; Lane 6: S. flexneri diluted by $10^2$ times; Lane 7: S. flexneri diluted by 1 times; Lane 8: S. boydii diluted by $10^2$ times; Lane 9: S. boydii diluted by $10^3$ times; Lane 10: sterile water; Lane 11: 100 bp marker.

*S. boydii* (ATCC 8700), *S. dysenteriae* (ATCC 4837), *S. flexneri* (ATCC 29903) and *S. sonnei* (ATCC 29930) were incubated in LB broth at 37° C. overnight. The resulting solution was diluted by $10^2$ and $10^3$ times with sterile water. 1 ml of the diluted solution was added to 50 ml water and then filtered by fluropore membrane. A PCR reaction was performed using IS1SS and IS1SR3 as primers and the resulting membrane as template. The PCR products were analyzed by gel electrophoresis. The resulting gel was dyed by ethidium bromide and observed under UV light. A control was prepared by adding 1 ml of sterile water to 50 ml water and conducted the PCR reaction as described above. As shown in FIG. 1, the samples of the *S. boydii, S. dysenteriae, S. flexneri* and *S. sonnei* diluted by $10^2$ and $10^3$ times have a band of 369 base pair DNA fragment in the gel (lanes 2–9) and the control does not have the band (lane 10).

Example 2

*Escherichia* W3110 (ATCC 27325), *Sallmonella choleraesuis* (ATCC 13311), *Klebsiella pneumoniae* (ATCC 13883) were incubated in LB broth at 37° C. overnight. *Serratia marcescens* (ATCC 13880) was incubated in LB broth at 25° C. overnight and *Enterobacter aerogenes* (ATCC 13048) and *Enterobacter cloacae* (ATCC 13047) were incubated in LB broth at 30° C. overnight. The resulting solutions were diluted by $10^2$ and $10^3$ times. 1 ml of the diluted solution was added to 50 ml water and then filtered by fluropore membrane. A PCR reaction was performed using IS1SS and IS1SR3 as primers and the resulting membrane as template. The PCR products were analyzed by gel electrophoresis. The resulting gel was dyed by ethidium bromide and observed under UV light. A control was prepared by adding 1 ml of sterile water to 50 ml water and conducted the PCR reaction as described above. As shown in FIG. 2, the sample of the *E. aerogenes* diluted by $10^3$ times or the sample of *E. coli* W3110 diluted by $10^2$ and $10^3$ times have a band of 369 base pair DNA fragment in the gel (lanes 11–13) and the sample of the *E. aerogenes* diluted by $10^2$ times, the samples of *Sallmonella choleraesuis* (ATCC 13311), *Klebsiella pneumoniae* (ATCC 13883), *Serratia marcescens* (ATCC 13880) and *Enterobacter cloacae* (ATCC 13047) and the control does not have the band (lanes 2–10 and lane 15).

Example 3

Figure 3:
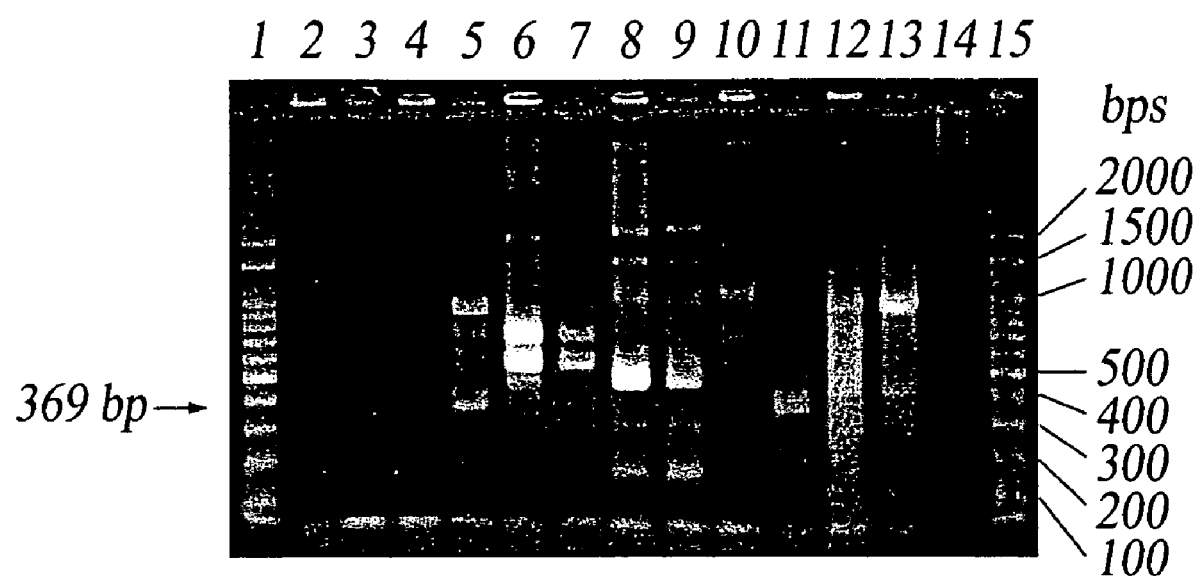
FIG. 3 shows the electrophoresis plot of the samples obtained from well water and incubated at 25° C.; Lane 1: 100 bp marker; Lane 2: *P. syclowiorum* diluted by $10^2$ times; Lane 3: *P. syclowiorum* diluted by $10^3$ times; Lane 4: *S. odorifera* diluted by $10^2$ times; Lane 5: *S. odorifera* diluted by $10^2$ times; Lane 6: *P. agglomerans* diluted by $10^2$ times; lane 7: *P. agglomerans* diluted by $10^3$ times; Lane 8: *E. hermanii* diluted by $10^2$ times; Lane 9: *E. hermanii* diluted by 1 times; Lane 10: *A. calcoacet/baumannii/gen* 2 diluted by $10^2$ times; Lane 11: *A. calcoacet/baumannii/gen* 2 diluted by $10^3$ times; Lane 12: *S. marcescens* diluted by $10^2$ times; Lane 13: *S. marcescens* diluted by $10^3$ times; Lane 14: sterile water; Lane 15: 100 bp marker.
Figure 4:
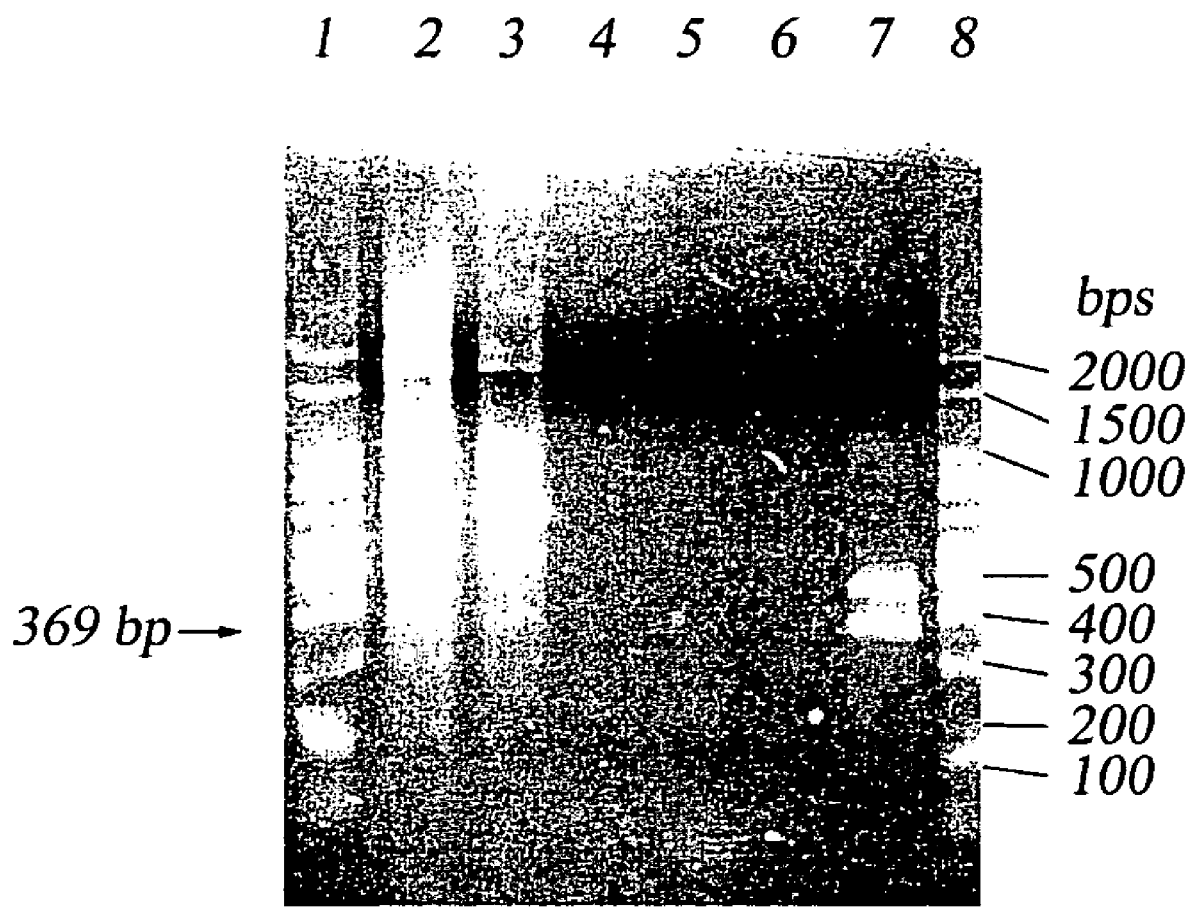
FIG. 4 shows the electrophoresis plot of the samples obtained from well water and incubated at 20° C.; Lane 1: 100 bp marker; Lane 2: *A. johnsonii* diluted by $10^2$ times; Lane 3: *A. johnsonii* diluted by $10^3$ times; Lane 4: *S. capitis* diluted by $10^2$ times; Lane 5: *S. capitis* diluted by $10^3$ times; Lane 6: water; Lane 7: *S. sonnei*; Lane 8: 100 bp marker.
Figure 5:
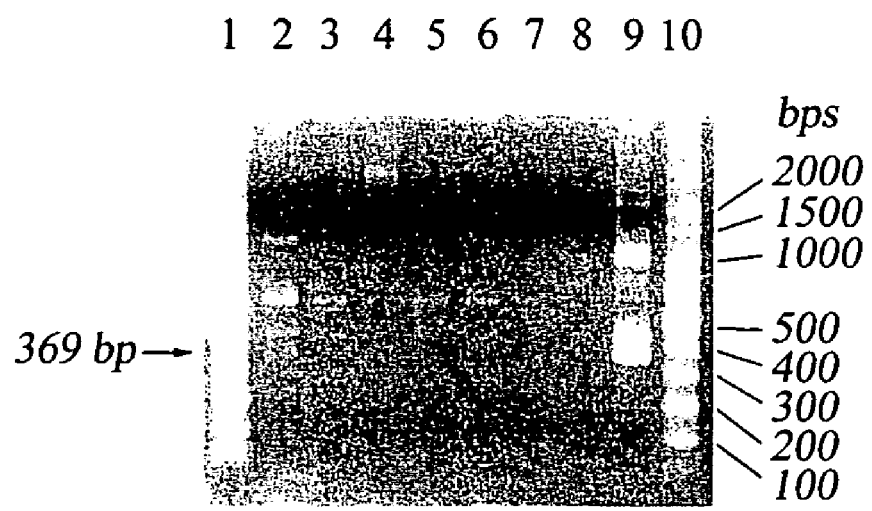
FIG. 5 shows the electrophoresis plot of the samples isolated from ground water and incubated at 25° C.; (A) Lane 1: 100 bp marker; Lane 2: *O. ureolytica/urethralis* diluted by $10^2$ times; Lane 3: *O. ureolytica/urethralis* diluted by $10^3$ times; Lane 4: *X. maltophilia* diluted by $10^2$ times; Lane 5: *X. maltophilia* diluted by $10^3$ times; Lane 6: the strain diluted by $10^2$ times that could not be identified; Lane 7: the strain diluted by $10^3$ times that could not be identified; Lane 8: sterile water; Lane 9: *S. sonnei* diluted by $10^2$ times; Lane 10: 100 bp marker; (B) Lane 1: 100 bp marker; Lane 2: *A. delafieldii* diluted by $10^2$ times; Lane 3: *A. delafieldii* diluted by $10^3$ times; Lane 4: the strain-1 diluted by $10^2$ times that was not identified; Lane 5: the strain-1 diluted by $10^3$ times that was not identified; Lane 6: *X. maltophilia* diluted by $10^2$ times; Lane 7: *X. maltophilia* diluted by $10^3$ times; Lane 8: *A. genospecies* 15 diluted by $10^2$ times; Lane 9: *A. genospecies* 15 diluted by $10^3$ times; Lane 10: the strain-2 diluted by $10^2$ times that was not identified; Lane 11: the strain-2 diluted by $10^3$ times that was not identified; Lane 12: *S. sonnei*; Lane 13: sterile water; Lane 14: 100 bp marker.
Figure 5:
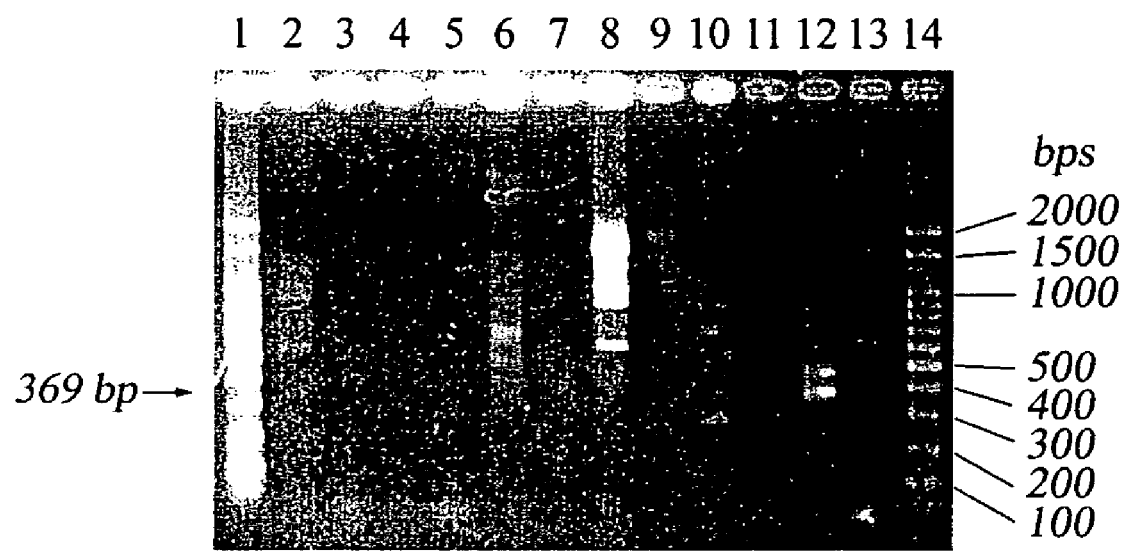

The ground water sample and well water sample were incubated in LB broth at 20° C. or 25° C. 16 strains were isolated from the samples and then identified. One strain cannot be identified and two strains were dead during the identification. Six strains, *P. syclowiorum, S. odorifera, P. agglomerans, E. hermanii, A. calcoacet/baumannii/gen 2* and *S. marcescens*, were identified from the well water incubated at 25° C. Two strains, *A. johnsonii* and *S. capitis*, were identified from the well water incubated at 20° C. Five strains, *O. ureolytica/urethralis, X. maltophilia, A. delafieldii, X. maltophilia* and *A. genospecies 15*, were identified from the ground water incubated at 25° C. The 16 strains were incubated in LB broth overnight. The resulting solutions were diluted with sterile water. The resulting solutions were diluted by $10^2$ and $10^3$ times. 1 ml of the diluted solution was added to 50 ml water and then filtered by fluropore membrane. A PCR reaction was performed using IS1SS and IS1SR3 as primers and the resulting membrane as template. The PCR products were analyzed by gel electrophoresis. The resulting gel was dyed by ethidium bromide and observed under UV light. A control was prepared by adding 1 ml of sterile water to 50 ml water and conducted the PCR reaction as described above. As shown in FIGS. 3, 4 and 5, the sample of the *S. odorifera* or *A. calcoacet/baumannii/gen* diluted by $10^3$ times and the sample of *S. marcescens* diluted by $10^2$ and $10^3$ times have a band of 369 base pair DNA fragment in the gel (lanes 5 and 11–13). The other samples and the control do not have the band.

Example 4

Figure 6:
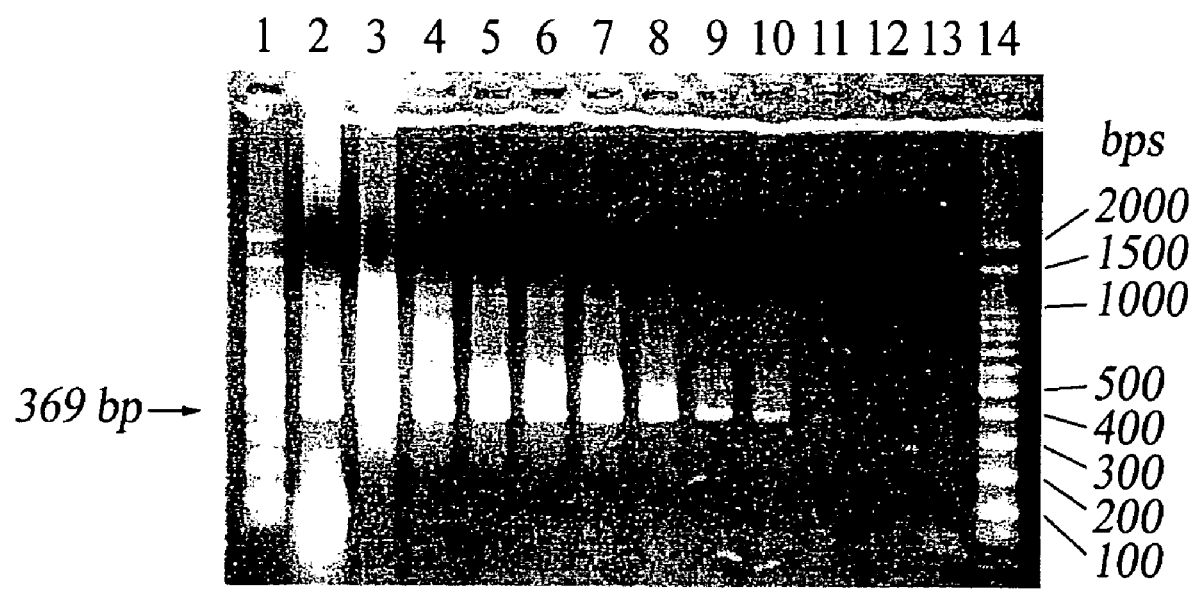
FIG. 6 shows the electrophoresis plot of *S. sonnei* (ATCC 29930) diluted by serial 10 times; Lane 1: 100 bp marker; Lane 2: dilution by 10 times; Lane 3: dilution by $10^2$ times; Lane 4: dilution by $10^3$ times; Lane 5: by $10^4$ times; Lane 6: dilution by $10^5$ times; Lane 7: dilution by $10^6$ times; Lane 8: dilution by $10^7$ times; Lane 9: dilution by $10^8$ times; Lane 10: dilution by $10^9$ times; Lane 11: dilution by $10^{10}$ times; Lane 12: dilution by $10^{11}$ times; Lane 13: sterile water; Lane 14: 100 bp marker.

*S. sonnei* (ATCC 29930) was incubated in LB broth at 37° C. overnight to $3.4 \times 10^{10}$ CFU/ml. The resulting solution was serially diluted by 10 to $10^{11}$ times. 1 ml of the diluted solution was added to 50 ml water and then filtered by fluropore membrane. A PCR reaction was performed using IS1SS and IS1SR3 as primers and the resulting membrane as template. The PCR products were analyzed by gel electrophoresis. The resulting gel was dyed by ethidium bromide and observed under UV light. A control was prepared by adding 1 ml of sterile water to 50 ml water and conducted the PCR reaction as described above. As shown in FIG. 6, the samples of the *S. sonnei* diluted by 10 to $10^{10}$ times have a band of 369 base pair DNA fragment in the gel (lanes 2–11) and the sample of the *S. sonnei* diluted by $10^{13}$ times and the control do not halve the band (lanes 2 and 13). Therefore, the *S. sonnei* could be detected as loon as the sample contained more than 3.4 cells. That is, the sensitivity of the method of the invention can reach 3.4 cells per sample.

Example 5

Figure 7:
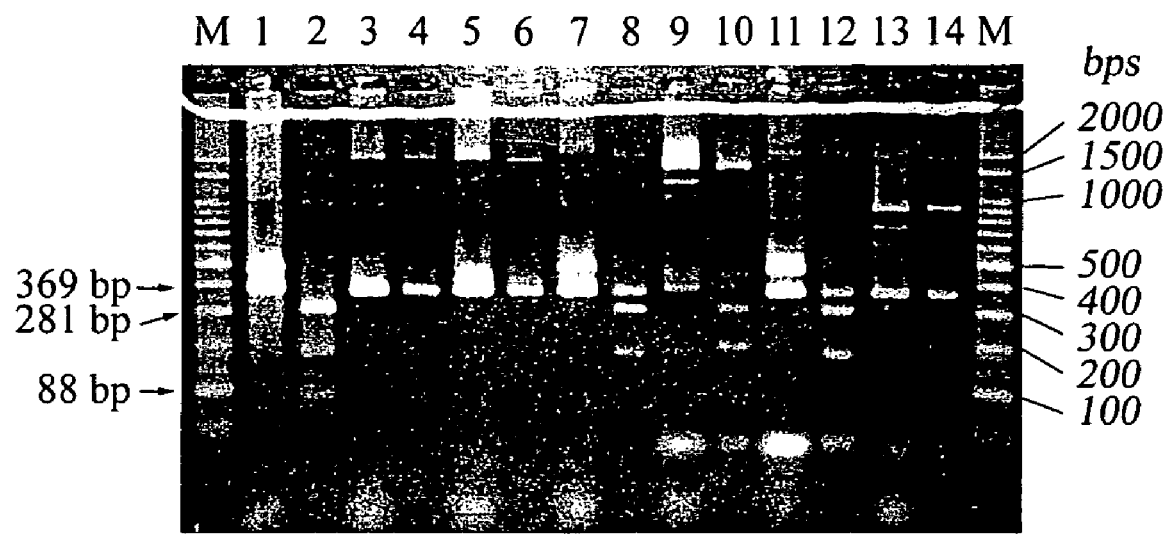
FIG. 7 shows the BstEII sliced fragments of the 369 bp PCR products of *S. boydii* (ATCC 8700), *S. dysenteriae* (ATCC 4837), *S. flexneri* (ATCC 29903), *S. sonnei* (ATCC 29930), *E. coli* W3110 (ATCC 27325), *E. aerogenes* (ATCC 13048), *S. odorifera*, *P. agglomerans* and *S. marcescens*; the lanes of odd numbers represent the PCR products that were not cut by the BstEII and the lanes of even numbers represent the PCR products that were cut by the BstEII; (A) Lane M: 100 bp marker; Lanes 1 and 2: *S. sonnei* (ATCC 19930); Lanes 3 and 4: *S. flexneri* (ATCC 29903); Lanes 5 and 6: *S. boydii* (ATCC 8700); Lanes 7 and 8: *S. dysenteriae* (ATCC 4837); Lanes 9 and 10: *E. aerogenes* (ATCC 13048); Lanes 11 and 12: *E. coli* W3110 (ATCC 27325); Lanes 13 and 14: *S. odorifera*; (B) Lanes 1 and 2: *Acinetobacter calcoacet/baumannii/gen* 2; Lanes 3 and 4: *S. marcescens*.
Figure 7:
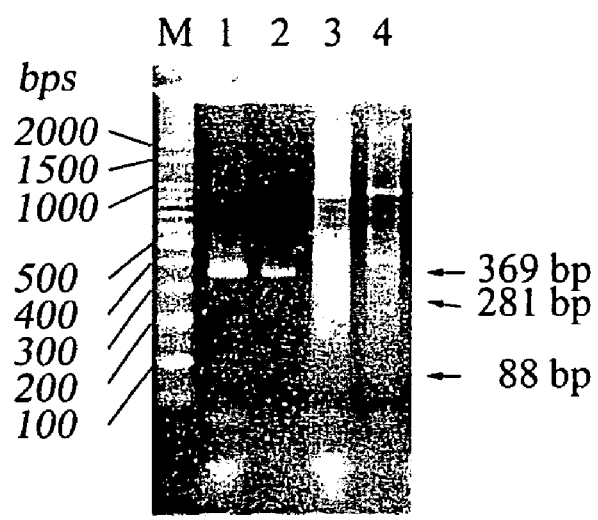

The 369 bp PCR products of *S. boydii* (ATCC 8700), *S. dysenteriae* (ATCC 4837), *S. flexneri* (ATCC 29903), *S. sonnei* (ATCC 29930), *E. coli* W3110 (ATCC 27325), *E. aerogenes* (ATCC 13048), *S. odorifera, P. agglomerans* and *S. marcescens* obtained in Examples 1 to 3 were sliced by restriction enzyme BstEII and then analyzed by gel electrophoresis. The resulting gel was dyed by ethidium bromide and observed under UV light. As shown in FIG. 7, only the 369 bp PCR product of *S. sonnei* (ATCC 29930) was sliced to 88bp and 281bp DNA fragments. The other strains did not produce the 88bp and 281 bp DNA fragments.

Example 6

Figure 8:
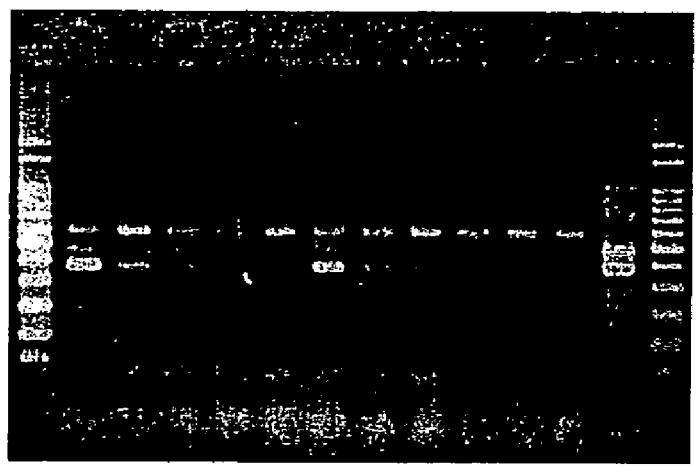
FIG. 8 shows the electrophoresis plot of the samples of *S. sonnei* ATCC 9290, ATCC 11060, ATCC 25931, ATCC 20920 and ATCC 29031; (a) Lane 1: 100 bp marker; Lane 2: *S. sonnei* ATCC 9290 diluted by $10^7$ times; Lane 3: *S. sonnei* ATCC 9290 diluted by $10^8$ times; Lane 4: *S. sonnei* ATCC 9290 diluted by $10^9$ times; Lane 5: *S. sonnei* ATCC 9290 diluted by $10^{10}$ times; Lane 6: *S. sonnei* ATCC 9290 diluted by $10^{11}$ times; Lane 7: *S. sonnei* ATCC 11060 diluted by $10^7$ times; Lane 8: *S. sonnei* ATCC 11060 diluted by $10^8$ times; Lane 9: *S. sonnei* ATCC 11060 diluted by $10^9$ times; Lane 10: *S. sonnei* ATCC 11060 diluted by $10^{10}$ times; Lane 11: *S. sonnei* ATCC 11060 diluted by $10^{11}$ times; Lane 12: sterile water; Lane 13: *S. sonnei* ; Lane 14: 100 bp marker; (b) Lane 1: 100 bp marker; Lane 2: *S. sonnei* ATCC 25931 diluted by $10^8$ times; Lane 3: *S. sonnei* ATCC 25931 diluted by $10^9$ times; Lane 4: *S. sonnei* ATCC 25931 diluted by $10^{10}$ times; Lane 5: *S. sonnei* ATCC 20920 diluted by $10^5$ times; Lane 6: *S. sonnei* ATCC 20920 diluted by $10^7$ times; Lane 7: *S. sonnei* ATCC 20920 diluted by $10^8$ times; Lane 8: *S. sonnei* ATCC 20920 diluted by $10^9$ times; Lane 9: *S. sonnei* ATCC 20920 diluted by $10^{10}$ times; Lane 10: sterile water; Lane 11: *S. sonnei* ATCC 29031 diluted by $10^8$ times; Lane 12: *S. sonnei* ATCC 29031 diluted by $10^9$ times; Lane 13: *S. sonnei* ATCC 29031 diluted by $10^{10}$ times; Lane 14: sterile water; Lane 15: *S. sonnei*; Lane 16: 100 bp marker.
Figure 8:
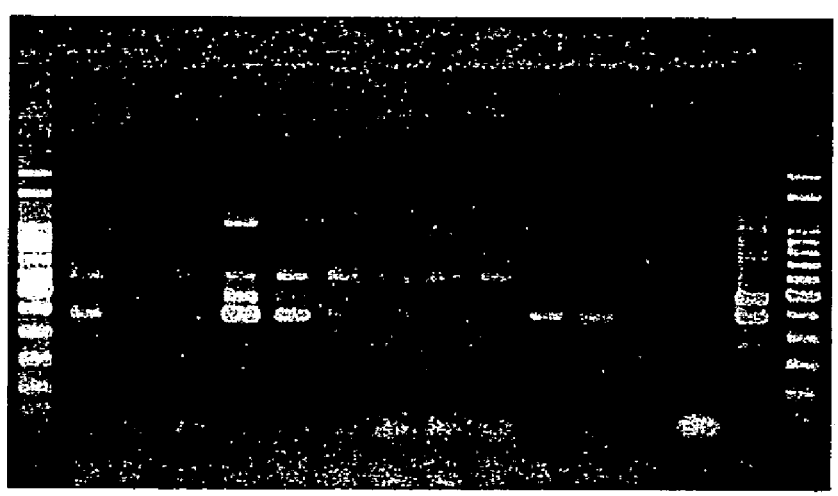
Figure 9:
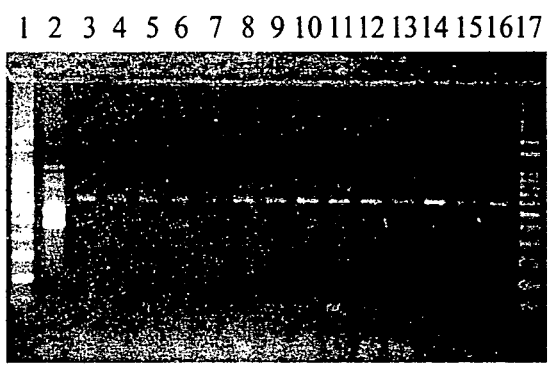
FIG. 9 shows the electrophoresis plots of the samples of *S. sonnei* SH 7105, SH 8255, SH 9397, SH 8069, SH 10567, South 27 and South 36 diluted by serial 10 times; (a) Lane 1: 100 bp marker; Lane 2: *S. sonnei* (ATCC 29930) diluted by $10^6$ times; Lane 3: *S. sonnei* (SH 7105) diluted by $10^8$ times; Lane 4: *S. sonnei* (SH 7105) diluted by $10^9$ times; Lane 5: *S. sonnei (SH* 7105) diluted by $10^{10}$ times; Lane 6: *S. sonnei* (SH 8255) diluted by $10^8$ times; Lane 7: *S. sonnei* (SH 8255) diluted by $10^9$ times; Lane 8: *S. sonnei* (SH 8255) diluted by $10^{10}$ times; Lane 9: sterile water; Lane 10: *S. sonnei* (SH 9397) diluted by $10^8$ times; Lane 11: *S. sonnei* (SH 9397) diluted by $10^9$ times; Lane 12: *S. sonnei* (SH 9397) diluted by $10^{10}$ times; Lane 13: *S. sonnei (SH* 8069) diluted by $10^8$ times; Lane 14: *S. sonnei* (SH 8069) diluted by $10^9$ times; Lane 15: *S. sonnei* (SH 8069) diluted by $10^{10}$ times; Lane 16: sterile-water; Lane 17: 100 bp marker; (b) Lane 1: 100 bp marker; Lane 2: *S. sonnei* (SH 10567) diluted by $10^7$ times; Lane 3: *S. sonnei* (SH 10567) diluted by $10^8$ times; Lane 4: *S. sonnei* (SH 10567) diluted by $10^9$ times; Lane 5: *S. sonnei* (SH 10567) diluted by $10^{10}$ times; Lane 6: *S. sonnei (SH* 10567) diluted by $10^{11}$times; Lane 7: *S. sonnei* (SH 10567) diluted by $10^{12}$ times; Lane 8: sterile water; Lane 9: *S. sonnei (ATCC* 29930) diluted by $10^6$ times; Lane 10: 100 bp marker; (c) Lane 1: 100 bp marker; Lane.2: *S. sonnei* (south 27) diluted by $10^6$ times; Lane 3: *S. sonnei* (south 27) diluted by $10^7$ times; Lane 4: *S. sonnei* (south 27) diluted by $10^8$ times; Lane 5: *S. sonnei* (south 27) diluted by $10^9$ times; Lane 6: *S. sonnei (south* 27) diluted by $10^{10}$times; Lane 7: *S. sonnei* (south 27) diluted by $10^{11}$ times; Lane 8: sterile water; Lane 9: *S. sonnei* (ATCC 29930) diluted by $10^6$ times; Lane 10: 100 bp marker; (d) Lane 1: 100 bp marker; Lane 2: *S. sonnei* (south 36) diluted by $10^9$ times; Lane 3: *S. sonnei* (south 36) diluted by $10^{10}$ times; Lane 4: *S. sonnei*
Figure 9:
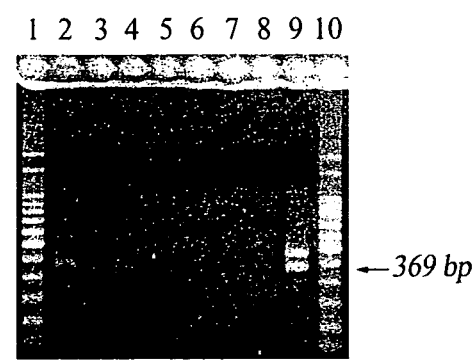
Figure 9:
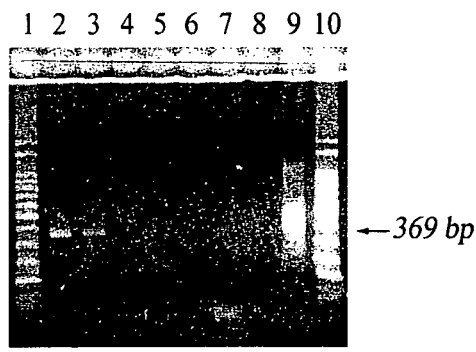
Figure 9:
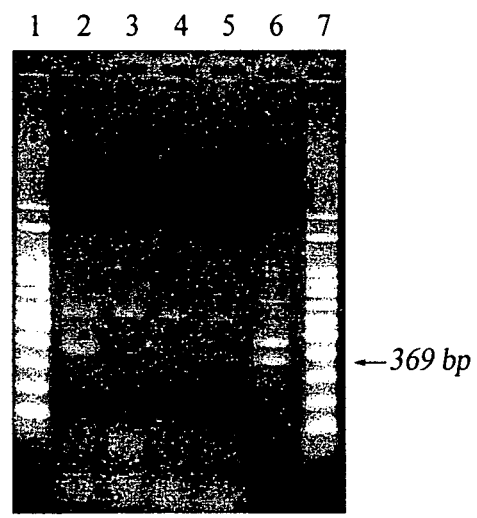

Five *S. sonnei* strains obtained from ATCC (American Type Culture Collection, Maryland, U.S.A), ATCC 9290, ATCC 11060, ATCC 25931, ATCC 20920 and ATCC 29031 and seven *S. sonnei* isolated from Taiwan, SH7105, SH8069, SH8255, SH10567, South 27 and South 26, were incubated in LB broth at 37° C. overnight and then diluted by serial 10 times. 1 ml of the diluted solution was added to 50 ml water and then filtered by fluropore membrane. A PCR reaction was performed using IS1SS and IS1SR3 as primers and the resulting membrane as template. The PCR products were analyzed by gel electrophoresis. The resulting gel was dyed by ethidium bromide and observed under UV light. A control was prepared by adding 1 ml of sterile water to 50 ml water and conducted the PCR reaction as described above. As shown in FIGS. 8 and 9, the samples of the twelve *S. sonnei* strains have a band of 369 base pair DNA fragment in the gel and the control does not have the band. The 369 bp PCR products were sliced by restriction enzyme BstEII and then analyzed by gel electrophoresis. As shown in FIG. 10, the twelve strains have 88 bp and 281 bp DNA fragments.

Example 7

*Shigella sonnei* was cultured in LB broth 37° C. overnight until the concentration reached $3.4 \times 10^{10}$ CFU/ml. Then, the medium was made with a series of dilutions (dilution factor of 10 to $10^{11}$ times). 1 ml of the diluted medium was added to 50ml of ground water. The resulting solution was passed through a fluorocarbon micropore filter membrane (FHLP, pore size: 0.5 µm, Millipore Co.) for filtration. The filter membrane was placed in sterile water and then shaken. The resulting solution was added with the primers (IS1SS and IS1SR3) and other PCR reagents, treated at a temperature of 95° C. for 5 minutes and then added with enzymes to perform a PCR reaction. 1 ml of sterile water was added to 50 ml of ground water as a control and the resulting solution was preformed with the above-mentioned steps and the PCR reaction.

The PCR products were analyzed with gel electrophoresis, dyed with ethidium bromide and then observed with UV light. As shown in FIG. 11, by using 10 to $10^{10}$ times dilution of *Shigella sonnei* (ATCC 29930) solution, bands of DNA are shown at 369 bp in the gel (lanes 2–11); however, when using $10^{11}$ times dilution, no DNA band are shown (lanes 12–13).

From the experiment, it can be determined that the method of the invention can successfully extract nucleic acid from microorganism in liquid samples and analyze microorganism in liquid samples by using specific primes in PCR reaction. Additionally, the method of the invention in combination with PCR assay has sensitivity in detecting 3.4 bacteria/sample for *Shigella sonnei* ATCC2930.

Example 8

Five strains of *Shigella sonnei* obtained from ATCC (ATCC 9290, ATCC 11060, ATCC 25931, ATCC 20920, and ATCC 29031) were cultured in LB broth at 37° C. overnight until they reached the concentration of $5.7 \times 10^9$ CFU/ml, $6 \times 10^9$ CFU/ml, $3 \times 10^8$ CFU/ml, $7.4 \times 10^9$ CFU/ml, and 3.7×

$10^9$ CFU/ml respectively. Then, the medium was made with a series of 10-fold dilutions (dilution factor of 10 to $10^{11}$ times). 1 ml of the diluted medium was added to 50 ml of ground water. The resulting solution was passed through a fluorocarbon micropore filter membrane (FHLP, pore size: 0.5 μm, Millipore Co.) for filtration. The filter membrane was placed in sterile water and then shaken. The resulting solution was added with the primers (IS1SS and IS1SR3) and other PCR reagents, treated at a temperature of 95° C. for 5 minutes and then added with enzymes to perform a PCR reaction. 1 ml of sterile water was added to 50 ml of ground water as a control and the resulting solution was preformed with the above-mentioned steps and the PCR reaction.

The PCR products were analyzed with gel electrophoresis, dyed with ethidium bromide and then observed with UV light. As shown in FIGS. 12(*a*) and (*b*), using $10^7$, $10^8$ and $10^9$ times dilution of *Shigella sonnei* ATCC 11060 solution, $10^8$ times dilution of *Shigella sonnei* ATCC 25931 solution, $10^6$, $10^7$ and $10^8$ times dilution of *Shigella sonnei* ATCC 20920 solution and $10^8$ and $10^9$ times dilution of *Shigella sonnei* ATCC 29031 solution, bands of DNA are shown at 369 bp in the gel (lanes 2, 3, 7, 8 and 9 in FIG. 2(*a*) and lanes 2, 5, 6, 7, 11 and 12 in FIG. 2(*b*).

From the experiment, it can be determined that the method of the invention can successfully extract nucleic acid from microorganism in liquid samples and analyze microorganism in liquid samples by using specific primes in PCR reaction. Additionally, the method of the invention in combination with PCR assay has sensitivity in detecting 57 bacteria/sample for *Shigella sonnei* ATCC9290, 6 bacteria/sample for *Shigella sonnei* ATCC11060, 3 bacteria/sample for *Shigella sonnei* ATCC25931, 74 bacteria/sample for *Shigella sonnei* ATCC20920 and 3.7 bacteria/sample for *Shigella sonnei* ATCC29031.

Example 9

Seven strains of *Shigella sonnei* isolated from Taiwan (SH 7105, SH 8069, SH 8255, SH 9397, SH 10567, south 27 and south 36) were cultured in LB broth at 37° C. for one night until they reached the concentration of $6.9 \times 10^9$ CFU/ml (SH 7105), $1.7 \times 10^9$ CFU/ml (SH 8069), $3.9 \times 10^9$ CFU/ml (SH 8255), $2.8 \times 10^8$ CFU/ml (SH 9397), $7.3 \times 10^8$ CFU/ml (SH 10567), $1.39 \times 10^9$ CFU/ml (south 27) and $8.1 \times 10^{10}$ CFU/ml (south 36) respectively. Then, the medium was made with a series of 10-fold dilutions. 1 ml of the diluted medium was added to 50 ml of ground water. The resulting solution was passed through a fluorocarbon micropore filter membrane (FHLP, pore size: 0.5 μm, Millipore Co.) for filtration. The filter membrane was placed in sterile water and then shaken. The resulting solution was added with the primers (IS1SS and IS1SR3) and other PCR reagents, treated at a temperature of 95° C. for 5 minutes and then added with enzymes to perform a PCR reaction. 1 ml of sterile water was added to 50 ml of ground water as a control and the resulting solution was preformed with the above-mentioned steps and the PCR reaction.

The PCR products were analyzed with gel electrophoresis, dyed with ethidium bromide and then observed with UV light. As shown in FIGS. 13(*a*) to (*d*), using $10^8$ times dilution of *Shigella sonnei* SH 8255 solution, $10^8$ times dilution of *Shigella sonnei* SH 9397 solution, $10^8$ times dilution of *Shigella sonnei* SH 8069 solution, $10^7$ or $10^8$ times dilution of *Shigella sonnei* SH 10567 solution, $10^6$, $10^7$ or $10^8$ times dilution of *Shigella sonnei* south 27 solution and $10^9$ or $10^{10}$ times dilution of *Shigella sonnei* south 36 solution, bands of DNA are shown at 369 bp in the gel (lanes 3, 6, 10 and 13 in FIG. 3(*a*), lanes 2 and 3 in FIG. 3(*b*), lanes 2 to 4 in FIG. 3(*c*) and lanes 2 and 3 in FIG. 3(*d*).

From the experiment, it can be determined that the method of the invention can successfully extract nucleic acid from microorganism in liquid samples and analyze microorganism in liquid samples by using specific primes in PCR reaction. Additionally, the method of the invention in combination with PCR assay has a senility in detecting 69 bacteria/sample for *Shigella sonnei* SH 7105, 17 bacteria/sample for *Shigella sonnei* SH 8069, 39 bacteria/sample for *Shigella sonnei* SH 8255, 2.3 bacteria/sample for *Shigella sonnei* SH 9397, 3.7 bacteria/sample for *Shigella sonnei* 10567, 13.9 bacteria/sample for *Shigella sonnei* south 27 and 8.1 bacteria/sample for *Shigella sonnei* south 36.

Example 10

The PCR products of the 5 strains purchased from ATCC of Example 2 and the 7 strains isolated from Taiwan of Example 3 were sliced with restriction enzyme BstEII, and analyzed with 1.5% agroase gel electrophoresis. FIG. 14 shows that the expected 78 bp and 291 bp DNA fragments can be obtained after the treatment of the PCR products of the above 12 bacteria with restriction enzyme BstEII.

What is claimed is:

1. A method for detecting *Shigella sonnei* in a solution sample, which comprises the following steps:
   (a) incubating said sample with primers IS1SS and IS1SR3 in a PCR reaction solution whereby a PCR reaction takes place which amplifies nucleic acids to produce a 369 base pair amplification product, wherein the primer IS1SS consists of SEQ ID NO: 1 and the primer IS1R3 consists of SEQ ID NO:2;
   (b) detecting the presence of a 369 base pair amplification product;
   (c) cutting the 369 base pair amplification product by restriction enzyme BstEII;
   (d) detecting the presence of the DNA fragments of the 78 base pair and 291 base pair; wherein the presence of said DNA fragments are indicative of the presence of *Shigella sonnie* in the sample.

2. The method according to claim 1, which, before the step (a), further comprises a step of filtering the solution sample with a membrane and treating the membrane at a temperature for a time period, that is sufficient to lyse the bacteria in said solution.

3. The method according to claim 2, wherein said temperature ranges from 85° C. to 97° C. and said time period ranges from 1 to 15 minutes.

4. The method according to claim 1, wherein the PCR product and the DNA fragments are detected by gel electrophoresis.

5. A method for extracting the nucleic acids of microorganisms from a solution sample, which comprises the following steps:
   (a) passing a solution sample through a filter membrane so that the microorganisms therein attach to the surface of the filter membrane;
   (b) placing the filter membrane to a solution;
   (c) heating the resulting solution to lyse the microorganisms so that their nucleic acids are released to the solution;
   (d) amplifying the nucleic acids in a PCR reaction with primers consisting of SEQ ID NO: 1 and SEQ ID NO: 2.

6. The method according to claim 5, wherein the filter membrane is further physically treated to improve the release of the microorganisms from the filter membrane to the solution.

7. The method according to claim 6, wherein the filter membrane is physically treated for 1 to 15 minutes.

8. The method according to claim 7, wherein the physical treatment is shaking.

9. The method according to claim 5, wherein the filter membrane is coated with a polyester of polytetrafluoroethylene.

10. The method according to claim 5, wherein the filter membrane is heated at a temperature from 85° C. to 97° C. for 1 to 15 minutes.

11. The method according to claim 5, wherein the microorganism is selected from the group consisting of *Escherichia. coli, Staphylococcus aureus, Salmonella* spp, *Vibrio. cholerae, Heliobacter pylori, Mycobacterium tuberculosis, Shigella sonnei, Legionelia* spp, *Pseudomonas aeruginosa* and *Enterovirus*.

12. The method according to claim 5, wherein the microorganism is *Shigella sonnei*.

* * * * *